(12) United States Patent
Mikami et al.

(10) Patent No.: US 11,259,693 B2
(45) Date of Patent: Mar. 1, 2022

(54) CABLE CONNECTION SUBSTRATE, IMAGING APPARATUS, ENDOSCOPE, AND METHOD OF MANUFACTURING IMAGING APPARATUS

(71) Applicant: OLYMPUS CORPORATION, Tokyo (JP)

(72) Inventors: Masato Mikami, Hachioji (JP); Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 621 days.

(21) Appl. No.: 16/174,879

(22) Filed: Oct. 30, 2018

(65) Prior Publication Data
US 2019/0069767 A1 Mar. 7, 2019

Related U.S. Application Data

(63) Continuation of application No. PCT/JP2016/064931, filed on May 19, 2016.

(51) Int. Cl.
*A61B 1/05* (2006.01)
*A61B 1/04* (2006.01)
*A61B 1/00* (2006.01)

(52) U.S. Cl.
CPC .......... *A61B 1/051* (2013.01); *A61B 1/00114* (2013.01); *A61B 1/04* (2013.01); *A61B 1/05* (2013.01)

(58) Field of Classification Search
CPC .................................................... A61B 1/051
See application file for complete search history.

(56) References Cited

U.S. PATENT DOCUMENTS

| 5,454,366 | A | * | 10/1995 | Ito | A61B 1/00096 |
| | | | | | 600/109 |
| 6,567,115 | B1 | * | 5/2003 | Miyashita | A61B 1/051 |
| | | | | | 348/76 |
| 2016/0028926 | A1 | | 1/2016 | Ichimura et al. | |

FOREIGN PATENT DOCUMENTS

| JP | 2002-291693 A | 10/2002 |
| JP | 2006-136488 A | 6/2006 |

(Continued)

OTHER PUBLICATIONS

International Search Report dated Jul. 26, 2016 issued in PCT/JP2016/064931.

(Continued)

*Primary Examiner* — Aaron B Fairchild
(74) *Attorney, Agent, or Firm* — Scully, Scott, Murphy & Presser, P.C.

(57) ABSTRACT

A cable connection substrate includes: a first substrate that is provided with, on a front surface of the first substrate, a first connection electrode to be connected to a sensor electrode of an imaging element, and provided with a second connection electrode on a back surface side of the first substrate; and a second substrate that is provided with, on a front surface of the second substrate, a third connection electrode to be connected to the second connection electrode, and provided with, on a top surface side of the second substrate, the top surface being a side surface perpendicular to the front surface of the second substrate, a plurality of cable connection electrodes to be connected to a plurality of cables. A sum of effective conductor areas of the plurality of cable connection electrodes is greater than a sum of effective conductor areas of the third connection electrode.

12 Claims, 12 Drawing Sheets

(56) References Cited

FOREIGN PATENT DOCUMENTS

| JP | 2007-234915 A | 9/2007 |
| JP | 2014-110847 A | 6/2014 |
| JP | 5775984 B1 | 9/2015 |
| JP | 2015-217162 A | 12/2015 |

OTHER PUBLICATIONS

Chinese Office Action dated Sep. 3, 2020 received in Chinese Patent Application No. 201680085812.8.

* cited by examiner

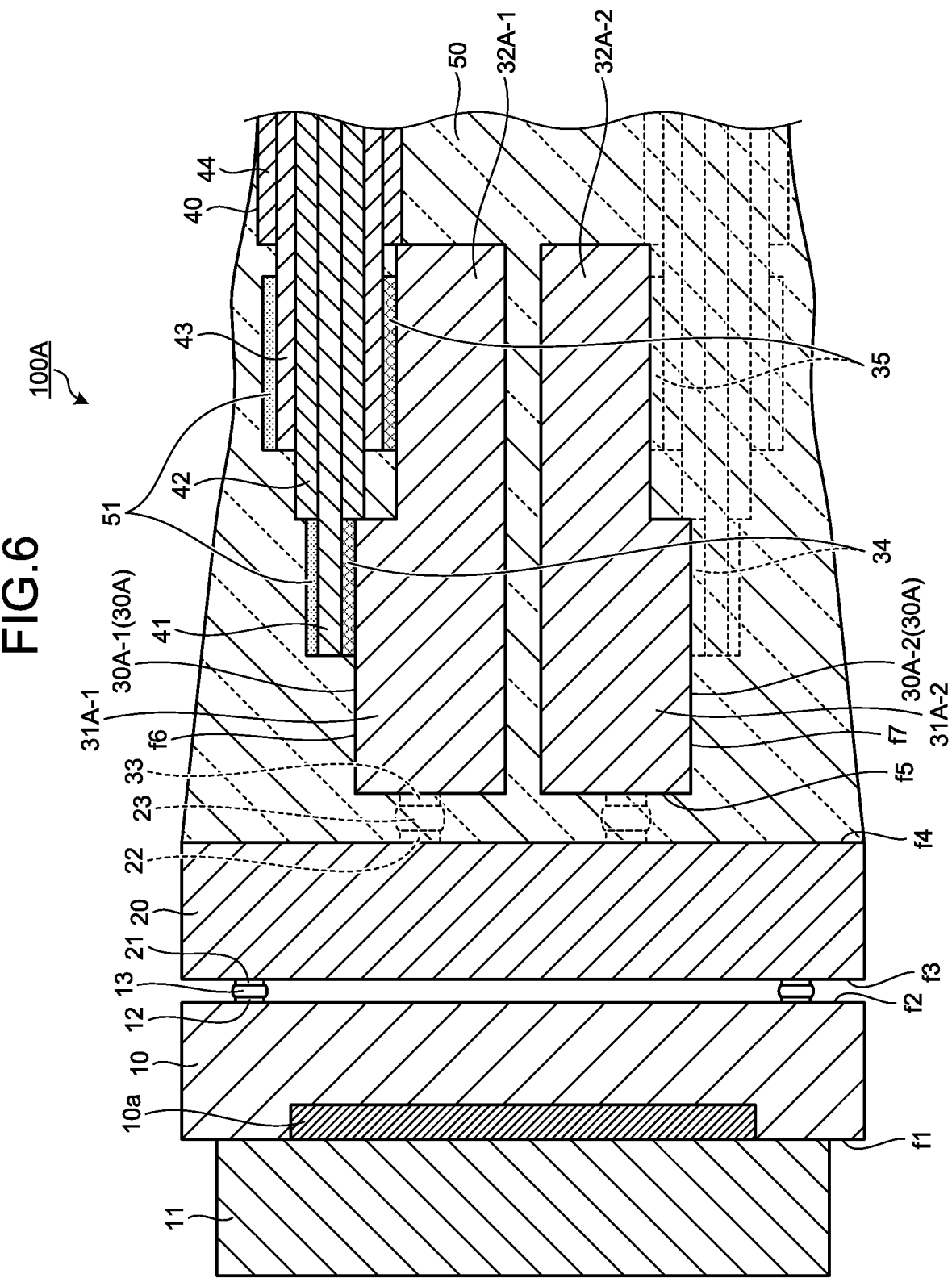

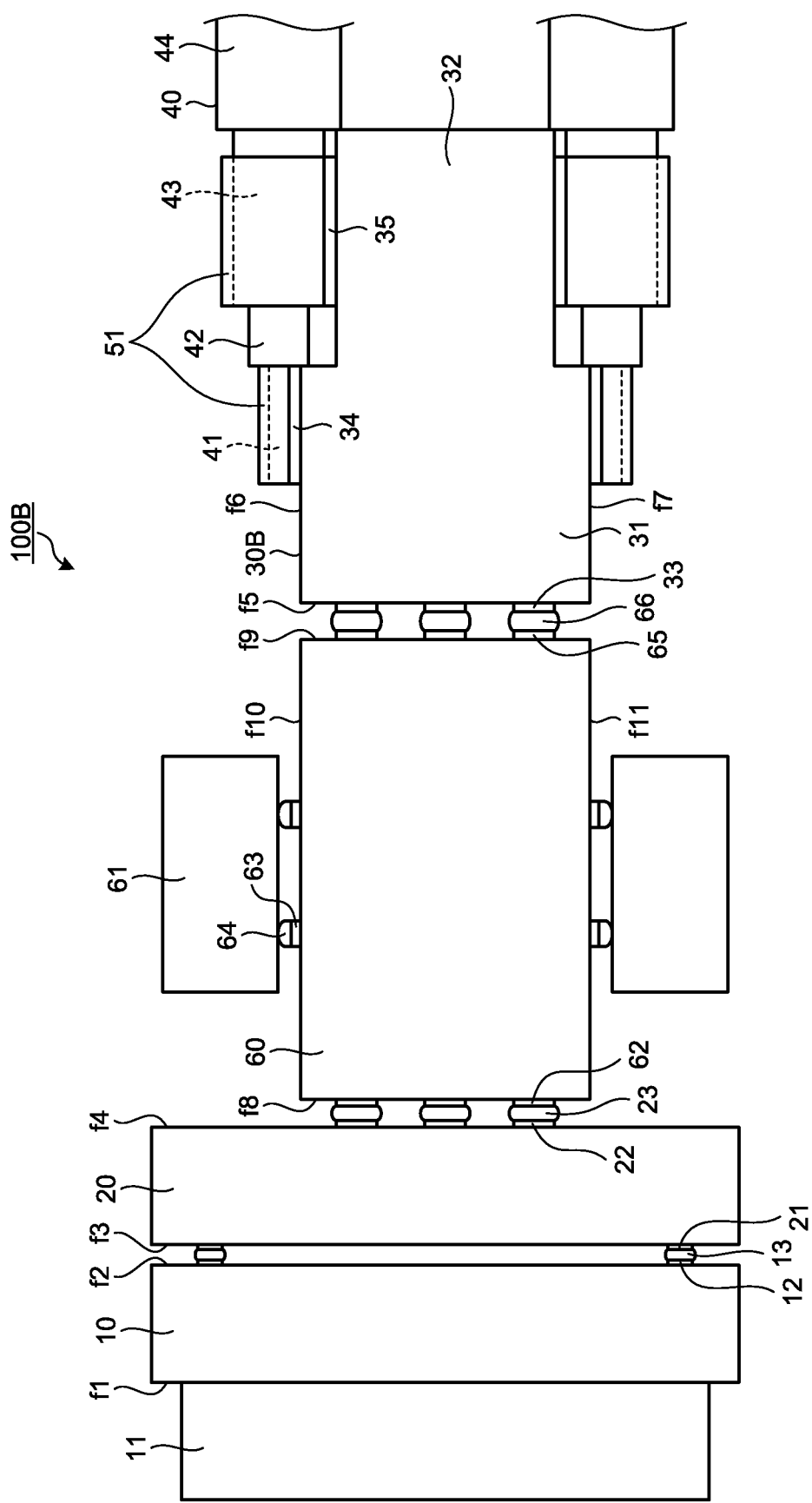

US 11,259,693 B2

CABLE CONNECTION SUBSTRATE, IMAGING APPARATUS, ENDOSCOPE, AND METHOD OF MANUFACTURING IMAGING APPARATUS

CROSS REFERENCES TO RELATED APPLICATIONS

This application is a continuation of PCT international application Ser. No. PCT/JP2016/064931 filed on May 19, 2016 which designates the United States, incorporated herein by reference.

BACKGROUND

1. Technical Field

The present disclosure relates to a cable connection substrate, an imaging apparatus, an endoscope, and a method of manufacturing an imaging apparatus.

2. Related Art

In the related art, an endoscope that is inserted into a subject and observes a subject region has been known and widely used in the medical field or the like. The endoscope is configured such that an imaging apparatus provided with an electronic component, such as an imaging element, is incorporated in a tip portion of a flexible elongated insertion tool.

In the endoscope, to ensure electrical property of the imaging element, it is desired to discharge heat that is generated by drive of the imaging element. As a technology for promptly discharging heat generated by the imaging element, an imaging apparatus has been proposed, in which a heat discharging member with a high thermal conductivity is arranged so as to come into contact with the imaging element (for example, see JP 2002-291693).

SUMMARY

In some embodiments, a cable connection substrate includes: a first substrate that is provided with, on a front surface of the first substrate, a first connection electrode to be connected to a sensor electrode of an imaging element, and provided with a second connection electrode on a back surface side of the first substrate; and a second substrate that is provided with, on a front surface of the second substrate, a third connection electrode to be connected to the second connection electrode, and provided with, on a top surface side of the second substrate, the top surface being a side surface perpendicular to the front surface of the second substrate, a plurality of cable connection electrodes to be connected to a plurality of cables. A sum of effective conductor areas of the plurality of cable connection electrodes is greater than a sum of effective conductor areas of the third connection electrode.

In some embodiments, an imaging apparatus includes: an imaging element that includes a light receiver configured to perform photoelectric conversion on incident light to generate an electrical signal, and a plurality of sensor electrodes provided on a back surface opposite to a surface on which the light receiver is provided; the cable connection substrate; and a plurality of cables. The cable connection substrate and the cables are positioned within a projection plane of a light receiving surface of the imaging element.

In some embodiments, an endoscope includes an insertion portion provided with the imaging apparatus at a distal end of the insertion portion.

In some embodiments, provided is a method of manufacturing the imaging apparatus. The method includes: connecting a plurality of cables to a plurality of cable connection electrodes of a second substrate that is provided with, on a front surface of the second substrate, a third connection electrode to be connected to the second connection electrode, and provided with, on a top surface side of the second substrate, the top surface being a side surface perpendicular to the front surface of the second substrate, the plurality of cable connection electrodes to be connected to a plurality of cables; and connecting, after the connecting the plurality of cables to the plurality of cable connection electrodes of the second substrate, the second substrate to a first substrate that has been connected to the imaging element.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a cross sectional view of an imaging apparatus according to a first modification of the present embodiment;

FIG. 8 is a side view of the imaging apparatus illustrated in FIG. 7;

DETAILED DESCRIPTION

In the following descriptions, as modes (hereinafter, referred to as "embodiments") for carrying out the disclosure, an endoscope system including an imaging apparatus will be described. In addition, the disclosure is not limited to the embodiments below. Further, in the description of the drawings, the same components are denoted by the same reference signs. Furthermore, it is necessary to note that the drawings are schematic, and relationships between thickness and width of each member, proportion of each member, and the like are different from reality. Moreover, portions having different dimensions and proportions are included among the drawings.

Figure 1:
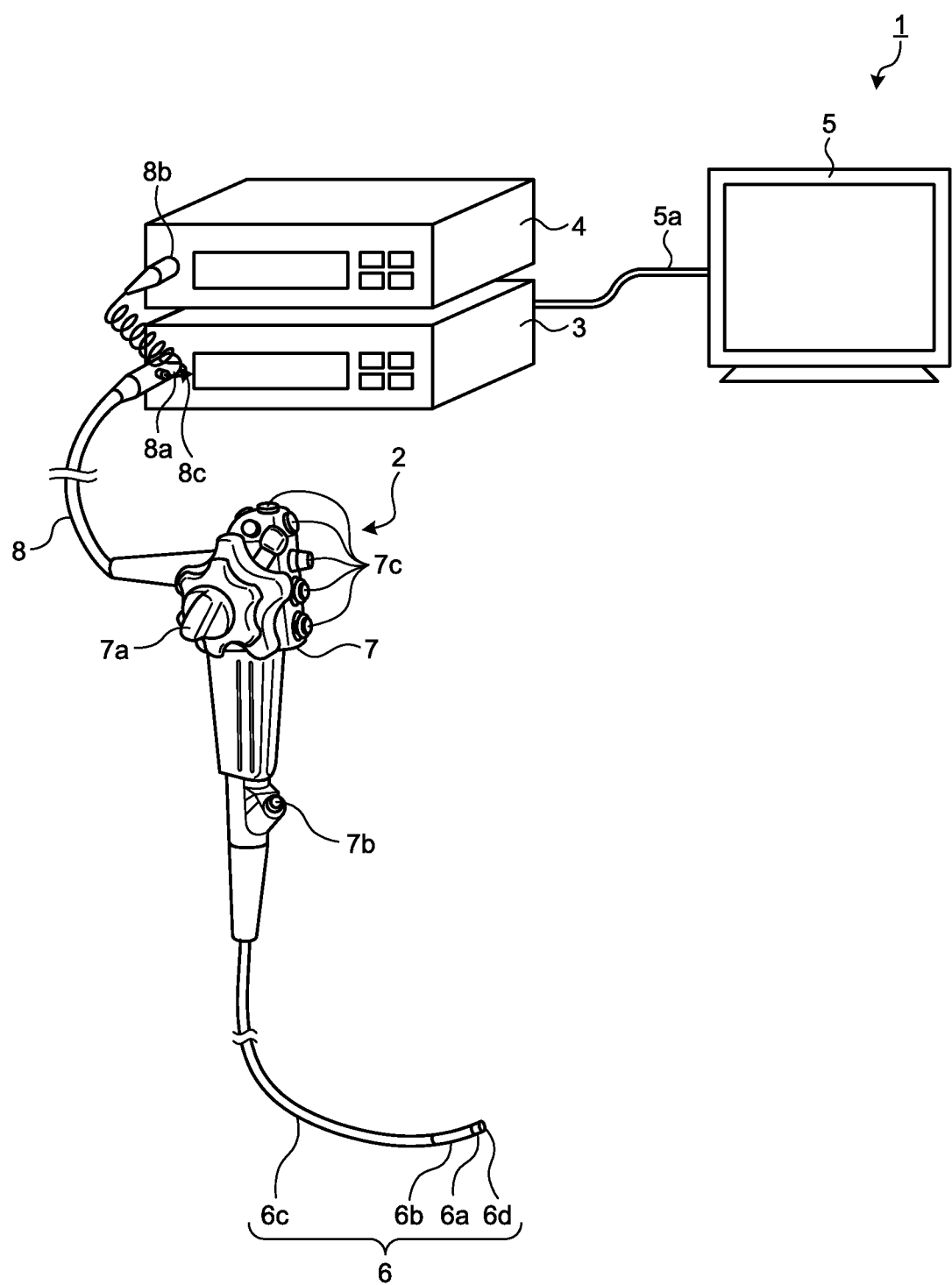
FIG. 1 is a diagram schematically illustrating an overall configuration of an endoscope system according to an embodiment.

FIG. 1 is a diagram schematically illustrating an overall configuration of an endoscope system according to an embodiment. As illustrated in FIG. 1, an endoscope system 1 according to the embodiment includes an endoscope 2 that captures an image inside a subject by being introduced into the subject and generates an image signal inside the subject, an information processing apparatus 3 (external processor) that performs predetermined image processing on the image signal captured by the endoscope 2 and controls each of units of the endoscope system 1, a light source device 4 that generates illumination light for the endoscope 2, and a display device 5 that displays an image of the image signal that is subjected to the image processing by the information processing apparatus 3.

The endoscope 2 includes an insertion portion 6 that is to be inserted into the subject, an operating unit 7 that is provided on a proximal end portion of the insertion portion 6 and to be held by an operator, and a flexible universal cord 8 that extends from the operating unit 7.

The insertion portion 6 is realized using an illumination fiber (light guide cable), an electrical cable, an optical fiber, and the like. The insertion portion 6 includes a tip portion 6a inside of which an imaging unit to be described later is provided, a bending portion 6b that is constituted of a plurality of bending pieces and is freely bendable, and a flexible tube portion 6c that is provided on a proximal end portion of the bending portion 6b and that has flexibility. In the tip portion 6a, an illumination unit that illuminates the inside of the subject via an illumination lens, an observation unit that captures an image inside the subject, an opening portion for communicating a treatment tool channel, and an air/water supply nozzle (not illustrated) are provided.

The operating unit 7 includes a bending knob 7a for causing the bending portion 6b to bend in a vertical direction and a horizontal direction, a treatment tool insertion portion 7b for inserting a treatment tool, such as a biopsy forceps or a laser scalpel, into a body cavity of a subject, and a plurality of switch portions 7c for operating the information processing apparatus 3, the light source device 4, and peripheral devices, such as an air supply device, a water supply device, and a gas supply device. The treatment tool inserted from the treatment tool insertion portion 7b comes out from an opening portion 6d at a distal end of the insertion portion 6 via an internally-provided treatment tool channel.

The universal cord 8 is realized using an illumination fiber, a cable, and the like. The universal cord 8 is bifurcated at a proximal end thereof, and an end portion of one of the branches serves as a connector 8a, and an end portion of the other one of the branches serves as a connector 8b. The connector 8a is detachably attached to a connector of the information processing apparatus 3. The connector 8b is detachably attached to the light source device 4. The universal cord 8 propagates illumination light emitted from the light source device 4 to the tip portion 6a via the connector 8b and the illumination fiber. Further, the universal cord 8 transfers an image signal captured by an imaging apparatus to be described later to the information processing apparatus 3 via a cable and the connector 8a.

The information processing apparatus 3 performs predetermined image processing on the image signal output from the connector 8a and controls the entire endoscope system 1.

The light source device 4 is realized using a light source that emits light, a condenser lens, and the like. The light source device 4 emits light from the light source and supplies the light, as illumination light for the inside of the subject adopted as an object, to the endoscope 2 that is connected via the connector 8b and the illumination fiber of the universal cord 8, under the control of the information processing apparatus 3.

The display device 5 is realized using a display made with liquid crystal, organic electro luminescence (EL), or the like. The display device 5 displays various kinds of information including an image subjected to the predetermined image processing by the information processing apparatus 3, via a video cable 5a. With this configuration, an operator is able to observe and determine behaviors of a desired position inside the subject by operating the endoscope 2 while viewing an image (in-vivo image) displayed by the display device 5.

Figure 2:
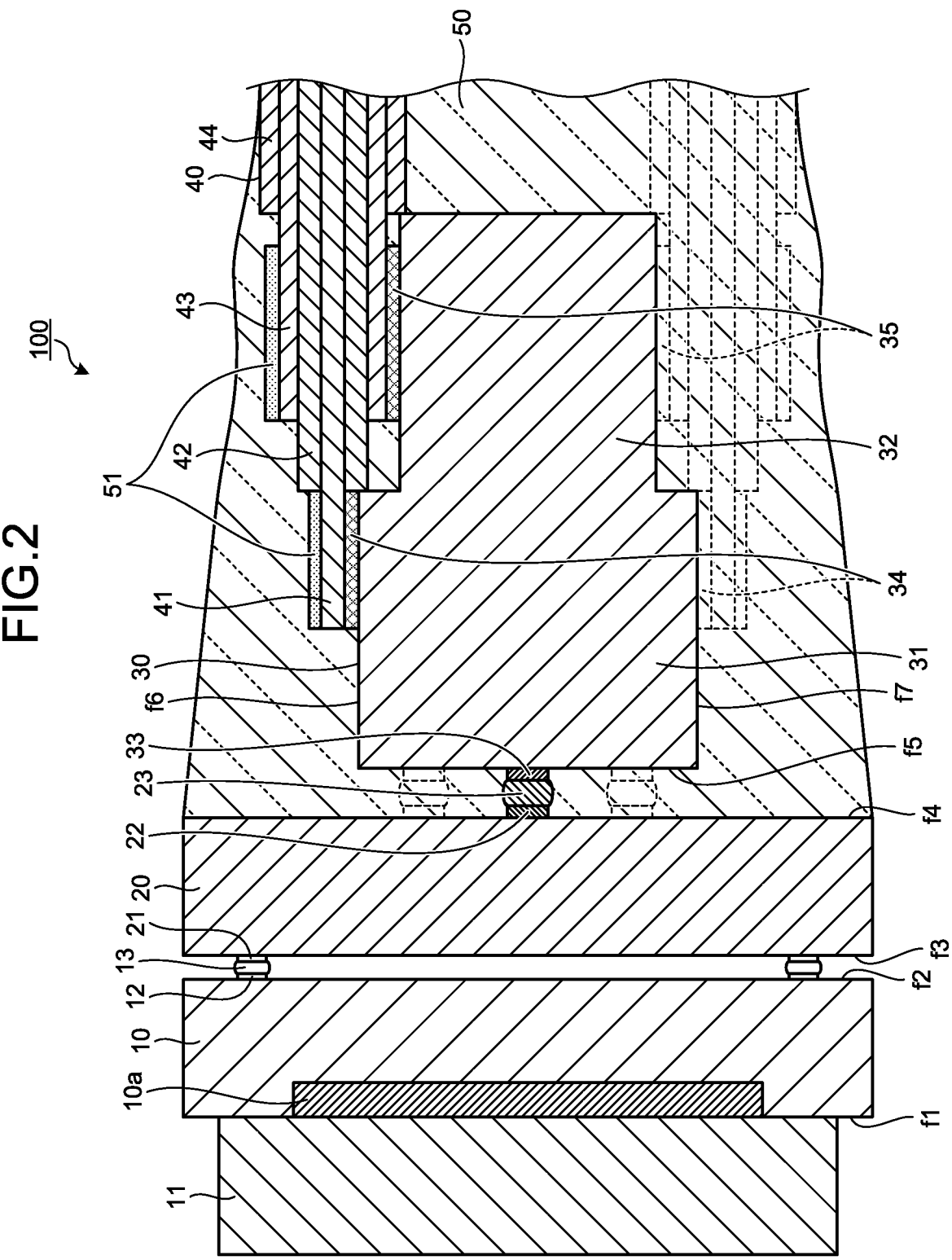
FIG. 2 is a cross sectional view of an imaging apparatus used in the endoscope illustrated in FIG. 1.
Figure 3:
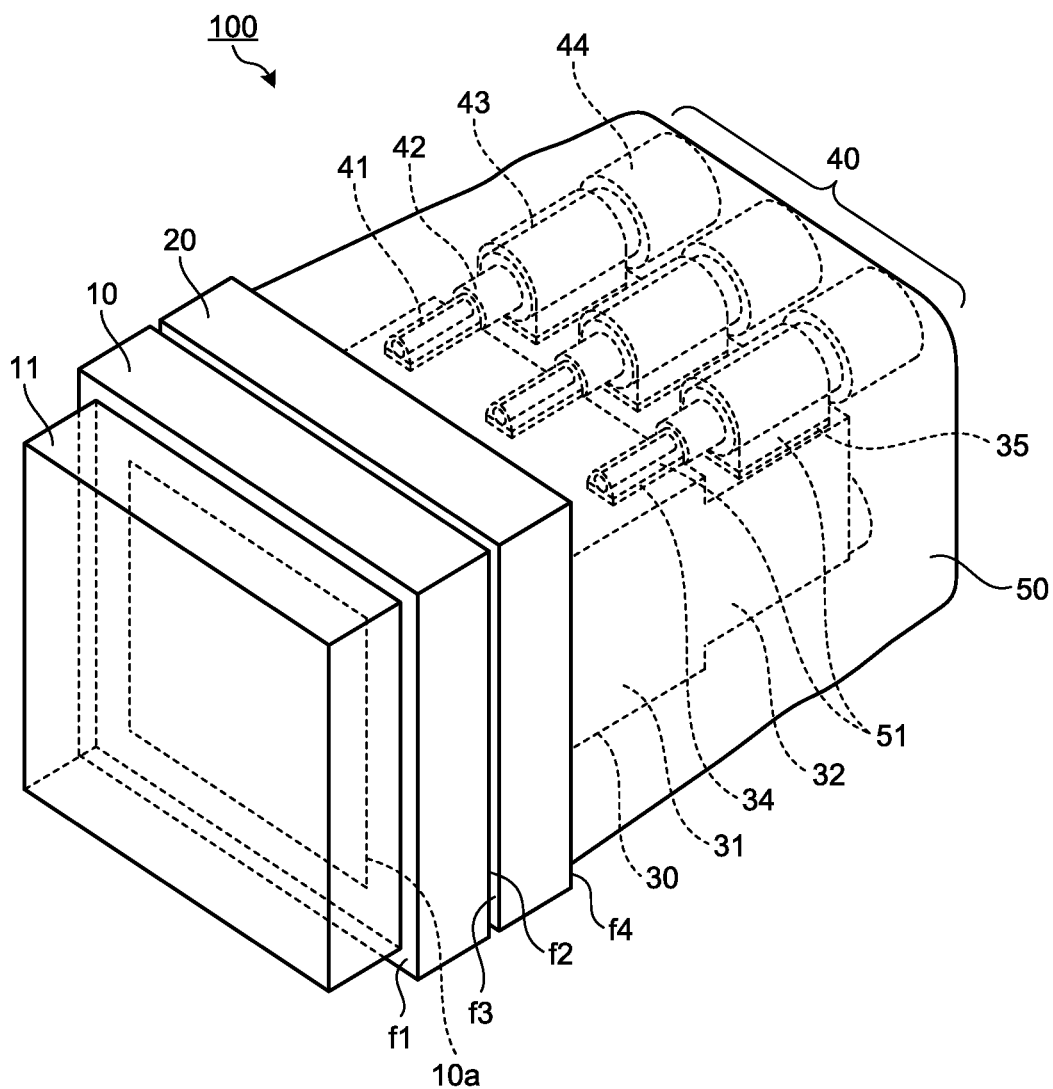
FIG. 3 is a perspective view of the imaging apparatus illustrated in FIG. 2.
Figure 4:
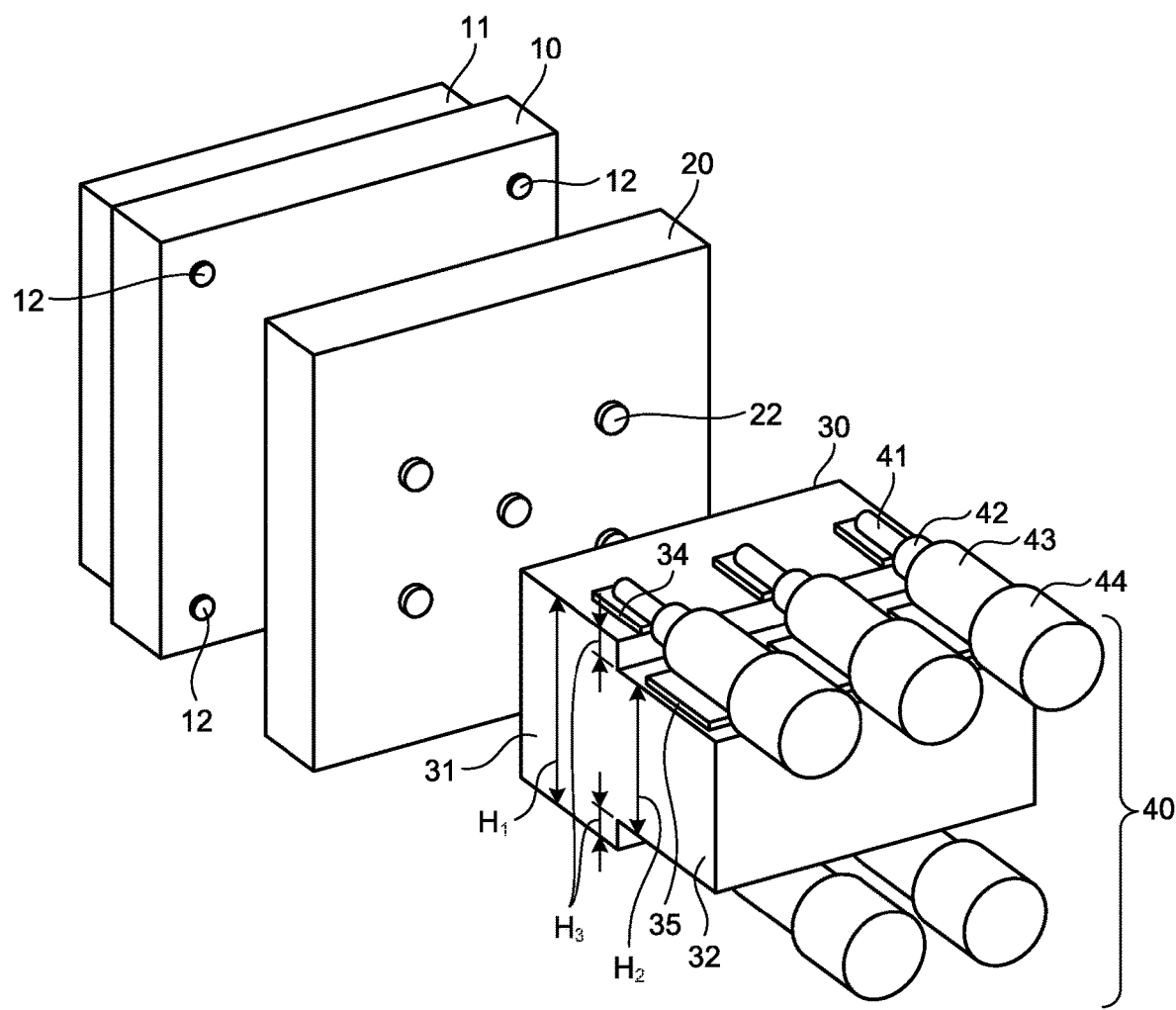
FIG. 4 is an exploded perspective view of the imaging apparatus illustrated in FIG. 2.

Next, a configuration of the imaging apparatus will be described in detail. FIG. 2 is a perspective view of the imaging apparatus used in the endoscope illustrated in FIG. 1. FIG. 3 is a perspective view of the imaging apparatus illustrated in FIG. 2. FIG. 4 is an exploded perspective view of the imaging apparatus illustrated in FIG. 2.

As illustrated in FIG. 2 to FIG. 4, an imaging apparatus 100 according to the first embodiment includes an imaging element 10, a first substrate 20, a second substrate 30, and a plurality of coaxial cables 40. In the present embodiment, a cable connection substrate is realized using the first substrate 20 and the second substrate 30.

A glass 11 is attached to a light receiving surface f1 that is a front surface of the imaging element 10. Light collected by a lens unit enters, via the glass 11, the light receiving surface f1 of the imaging element 10 that includes a light receiving unit 10a. Sensor electrodes 12 are provided at four respective corners on a back surface f2 side opposite to the light receiving surface f1 of the imaging element 10.

The first substrate 20 has an approximately same plate shape as that of the imaging element 10. On a front surface f3 side that comes into contact with the imaging element 10, first connection electrodes 21 are provided at positions facing the sensor electrodes 12, and are electrically and mechanically connected to the sensor electrodes 12 via bumps 13. On a back surface f4 side of the first substrate 20, second connection electrodes 22 are provided at connection positions of the second substrate 30.

The second substrate 30 includes a first main body portion 31 and a second main body portion 32. In the first main body portion 31, third connection electrodes 33 are provided on a front surface f5 side that comes into contact with the first substrate 20, and electrically and mechanically connected to the second connection electrodes 22 of the first substrate 20 via bumps 23. Meanwhile, a sum of effective conductor areas of the second connection electrodes 22 is approximately equal to that of the third connection electrodes 33. Here, the effective conductor area means an area of each of connection electrode surfaces that function for electrical and mechanical connection. On a top surface f6 and a bottom surface f7 serving as side surfaces perpendicular to the front surface f5 of the first main body portion 31, core wire connection electrodes 34 are provided and core wires 41 of the coaxial cables 40 to be described later are connected via solders 51. Further, on the top surface f6 and the bottom surface f7 serving as side surfaces perpendicular to the front surface f5 of the second main body portion 32, shield connection electrodes 35 are provided and shields 43 of the coaxial cables 40 to be described later are connected via the solders 51. In the present embodiment, a cable connection electrode is constituted of the core wire connection electrode 34 and the shield connection electrode 35.

The second main body portion 32 is thinner than the first main body portion 31, that is, a height $H_1$ of the first main body portion 31 (the length between the top surface f6 and the bottom surface f7) is higher than a height $H_2$ of the second main body portion 32 (the length between the top surface f6 and the bottom surface f7). In other words, the second substrate 30 is positioned within a projection plane of the front surface f3 of the first substrate 20. In addition, it is preferable that a height $H_3$ of a stepped portion between the first main body portion 31 and the second main body portion 32 is set to be approximately equal to a sum of thicknesses of an internal insulator 42 and the shield 43. With this configuration, it is possible to connect the core wires 41 to the core wire connection electrodes 34 without folding the core wires 41.

The coaxial cable 40 includes the core wire 41 made of a conductive material, the internal insulator 42 that covers an outer circumference of the core wire 41, the shield 43 that covers an outer circumference of the internal insulator 42, and an external insulator 44 that covers an outer circumference of the shield 43. An end portion of the coaxial cable 40 on the side connected to the second substrate 30 is processed such that the core wire 41, the internal insulator 42, and the shield 43 are exposed in a stepwise manner from the tip portion. The exposed core wire 41 and the shield 43 are connected to the core wire connection electrode 34 and the shield connection electrode 35, respectively.

A connection portion between the first substrate 20 and the second substrate 30 is sealed with a sealing resin 50. It is preferable to use, as the sealing resin 50, an insulating material with a high thermal conductivity of 0.2 mW/m/K or higher. In addition, a circumference of connection portions between the coaxial cables 40 and each of the core wire connection electrodes 34 and the shield connection electrodes 35 are sealed with the sealing resin 50 with a high thermal conductivity. Heat discharged from the imaging element 10 is mainly discharged via the electrode portions with high thermal conductivities, that is, the sensor electrodes 12, the bumps 13, the first connection electrodes 21, wiring portions (not illustrated) inside the first substrate 20, the second connection electrodes 22, the bumps 23, the third connection electrodes 33, wiring portions (not illustrated) inside the second substrate 30, and the coaxial cables 40; however, by sealing the connection portion between the first substrate 20 and the second substrate 30 and sealing the circumferences of the connection portions between the cable connection electrodes and the coaxial cables 40 with the sealing resin 50 with a high thermal conductivity, it becomes possible to discharge a greater amount of heat via the sealing resin 50 in addition to the electrode portions as described above.

In the imaging apparatus 100, a sum of effective conductor areas of the second connection electrodes 22 is set to be greater than a sum of effective conductor areas of the first connection electrodes 21. Further, a sum of effective conductor areas of the core wire connection electrodes 34 and the shield connection electrodes 35 is set to be greater than a sum of effective conductor areas of the third connection electrodes 33. By increasing the areas of the electrode portions with high thermal conductivities on a proximal end portion (on the side connected to the coaxial cables 40), heat generated by the imaging element 10 is likely to be discharged to the proximal end portion side while heat from the proximal end portion side is less likely to be transmitted; therefore, it is possible to reduce a thermal influence on the imaging element 10. Furthermore, the sum of the effective conductor areas of the core wire connection electrodes 34 and the shield connection electrodes 35 is greater than the sum of the effective conductor areas of the third connection electrodes 33 (the sum of the effective conductor areas of the second connection electrodes 22), and the sum of the effective conductor areas of the third connection electrodes 33 (the sum of the effective conductor areas of the second connection electrodes 22) is greater than the sum of the effective conductor areas of the first connection electrodes 21, and, this configuration is preferable for transferring electrical signals.

Moreover, it is preferable that a contact area of the second substrate 30 and the sealing resin 50 on the front surface f5 of the second substrate 30 is greater than the sum of the effective conductor areas of the third connection electrodes 33. By setting the contact area of the second substrate 30 and the sealing resin 50 to be greater than the sum of the effective conductor areas of the third connection electrodes 33, it becomes possible to improve a connection strength between the first substrate 20 and the second substrate 30 and increase a heat transfer area, so that it becomes possible to discharge a large amount of heat.

In the imaging apparatus 100, the first substrate 20, the second substrate 30, the coaxial cables 40, and the sealing resin 50 are positioned within a projection plane of the light receiving surface f1 of the imaging element 10. In other words, the first substrate 20, the second substrate 30, the coaxial cables 40, and the sealing resin 50 have sizes that fall within the projection plane of the light receiving surface f1 of the imaging element 10. With this configuration, it is possible to reduce a diameter of the imaging apparatus 100.

Next, a method of manufacturing the imaging apparatus 100 will be described with reference to the drawings. FIG. 5A to FIG. 5D are diagrams for explaining the process of manufacturing the imaging apparatus 100.

Figure 5A:
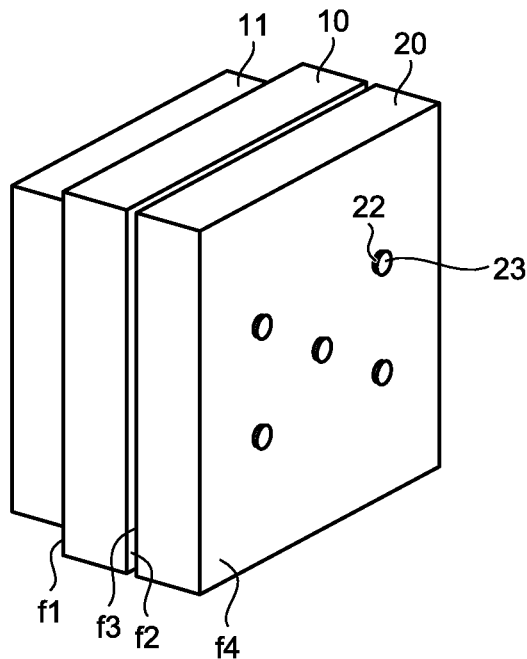
FIG. 5A is a diagram for explaining a process of manufacturing the imaging apparatus illustrated in FIG. 2.

As illustrated in FIG. 5A, the sensor electrodes 12 provided on the back surface f2 of the imaging element 10 in which the glass 11 is attached to the light receiving surface f1 are connected to the first connection electrodes 21 of the front surface f3 of the first substrate 20 via the bumps 13. After the connection, the bumps 23 are formed on the second connection electrodes 22 on the back surface f4 of the first substrate 20.

Figure 5B:
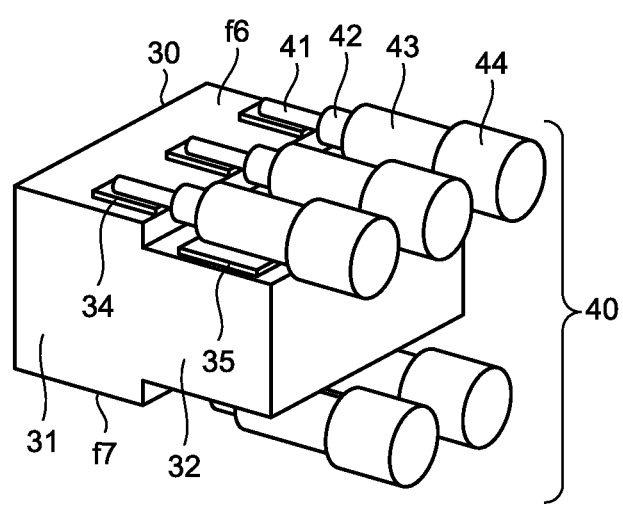
FIG. 5B is a diagram for explaining the process of manufacturing the imaging apparatus illustrated in FIG. 2.

As illustrated in FIG. 5B, the positions of the coaxial cables 40 are determined on the top surface f6 and the bottom surface f7 of the second substrate 30, and thereafter, the core wires 41 and the shields 43 are connected to the core wire connection electrodes 34 and the shield connection electrodes 35 by the solders 51.

Figure 5C:
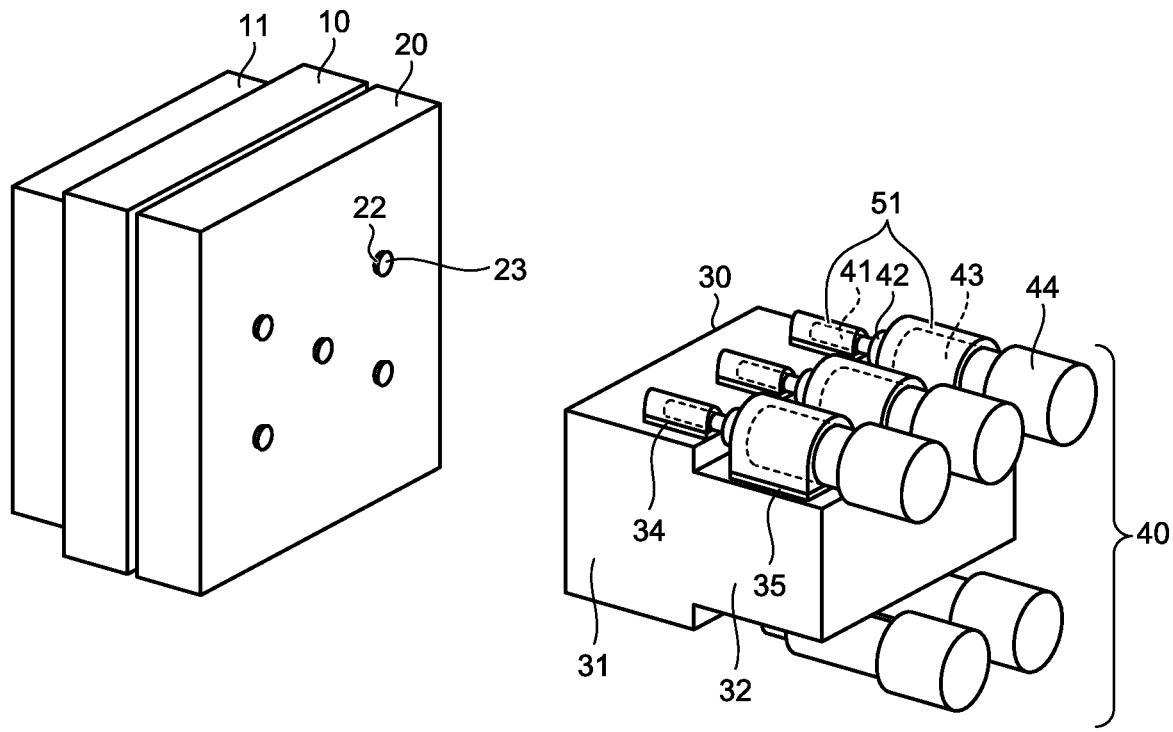
FIG. 5C is a diagram for explaining the process of manufacturing the imaging apparatus illustrated in FIG. 2.

As illustrated in FIG. 5C, the first substrate 20 that has been connected to the imaging element 10 is connected to the second substrate 30 that has been connected to the coaxial cables 40. The first substrate 20 and the second substrate 30 are connected via the bumps 23 after the positions of the second connection electrodes 22 and the third connection electrodes 33 are aligned.

Figure 5D:
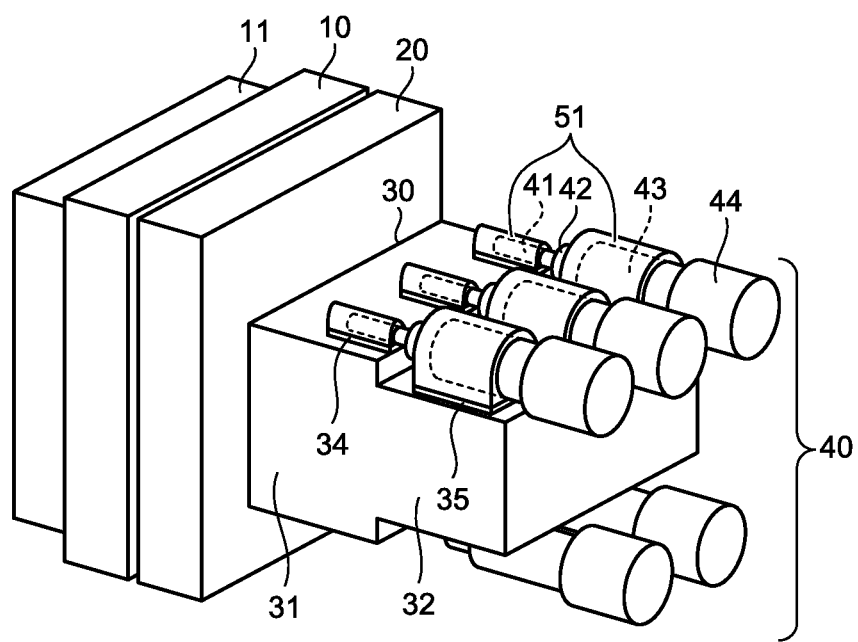
FIG. 5D is a diagram for explaining the process of manufacturing the imaging apparatus illustrated in FIG. 2.

As illustrated in FIG. 5D, after the first substrate 20 and the second substrate 30 are connected to each other, the connection portion between the first substrate 20 and the second substrate 30 and the peripheries of the connection portions between the coaxial cables 40 and each of the core wire connection electrodes 34 and the shield connection electrodes 35 are sealed with the sealing resin 50.

In the present embodiment, three connection processes of (1) connection between the imaging element 10 and the first substrate 20, (2) connection between the first substrate 20 and the second substrate 30, and (3) connection between the second substrate 30 and the coaxial cables 40 are included. Among these processes, (3) connection between the second substrate 30 and the coaxial cable 40 needs a long heating time to melt the solders, and therefore has a large thermal influence on an imaging element 10. By connecting the first substrate 20 that has been connected to the imaging element 10 and the second substrate 30 that has been connected to the coaxial cable 40 after completion of (3) connection between the second substrate 30 and the coaxial cables 40, it is possible to reduce a thermal influence on the imaging element 10.

Further, although the imaging element 10 is thermally influenced due to heating when the first substrate 20 that has been connected to the imaging element 10 is connected to the second substrate 30 that has been connected to the coaxial cables 40, because the sum of the effective conductor areas of the second connection electrodes 22 is greater than the sum of the effective conductor areas of the first connection electrodes 21, and because the sum of the effective conductor areas of the core wire connection electrodes 34 and the shield connection electrodes 35 is greater than the sum of the effective conductor areas of the third connection electrodes 33, the heat applied during connection of the first substrate 20 and the second substrate 30 is transferred to the proximal end side on which a large effective conductor area is provided, that is, on the coaxial cables 40 side, so that it is possible to reduce a thermal influence on the imaging element 10.

Meanwhile, the imaging apparatus 100 may be manufactured by performing (2) connection between the first substrate 20 and the second substrate 30, (3) connection between the second substrate 30 and the coaxial cables 40, and (1) connection between the imaging element 10 and the first substrate 20 in this order. Even through the processes as described above, it is possible to reduce a thermal influence on the imaging element 10.

First Modification

FIG. 6 is a cross sectional view of an imaging apparatus according to a first modification of the present embodiment. In an imaging apparatus 100A according to the first modification, a second substrate 30A includes a substrate 30A-1 and a substrate 30A-2. The substrate 30A-1 and the substrate 30A-2 are substrates obtained by vertically dividing the second substrate 30 of the embodiment.

The substrate 30A-1 includes a first main body portion 31A-1 and a second main body portion 32A-1, and the substrate 30A-2 includes a first main body portion 31A-2 and a second main body portion 32A-2. In the first main body portions 31A-1 and 31A-2, the third connection electrodes 33 are provided on the front surface f5 side, and the core wire connection electrodes 34 are provided on the top surface f6 or the bottom surface f7. Further, the shield connection electrodes 35 are provided on the top surface f6 or the bottom surface f7 of the second main body portions 32A-1 and 32A-2. A space between the substrate 30A-1 and the substrate 30A-2 is filled with the sealing resin 50.

The imaging apparatus 100A according to the first modification is configured such that, similarly to the embodiment, the sum of the effective conductor areas of the second connection electrodes 22 is greater than the sum of the effective conductor areas of the first connection electrodes 21, and the sum of the effective conductor areas of the core wire connection electrodes 34 and the shield connection electrodes 35 is greater than the sum of the effective conductor areas of the third connection electrodes 33. Therefore, heat generated by the imaging element 10 is likely to be discharged to the proximal end portion side while heat from the proximal end portion side is less likely to be transmitted, so that it is possible to reduce a thermal influence on the imaging element 10.

In addition, in the imaging apparatus 100A, the first substrate 20, the second substrate 30A, the coaxial cables 40, and the sealing resin 50 are positioned within the projection plane of the light receiving surface f1 of the imaging element 10. In other words, the first substrate 20, the second substrate 30A, the coaxial cables 40, and the sealing resin 50 have sizes that fall within the projection plane of the light receiving surface f1 of the imaging element 10. With this configuration, it is possible to reduce a diameter of the imaging apparatus 100A. In the imaging apparatus 100A, each of the substrate 30A-1 and the substrate 30A-2 is connected to the imaging element 10 that has been connected to the first substrate 20. By connecting, through two separate processes, the substrate 30A-1 and the substrate 30A-2 that constitute the second substrate 30A, it is possible to reduce a maximum load of the amount of heat applied to the imaging element 10.

Second Modification

Figure 7:
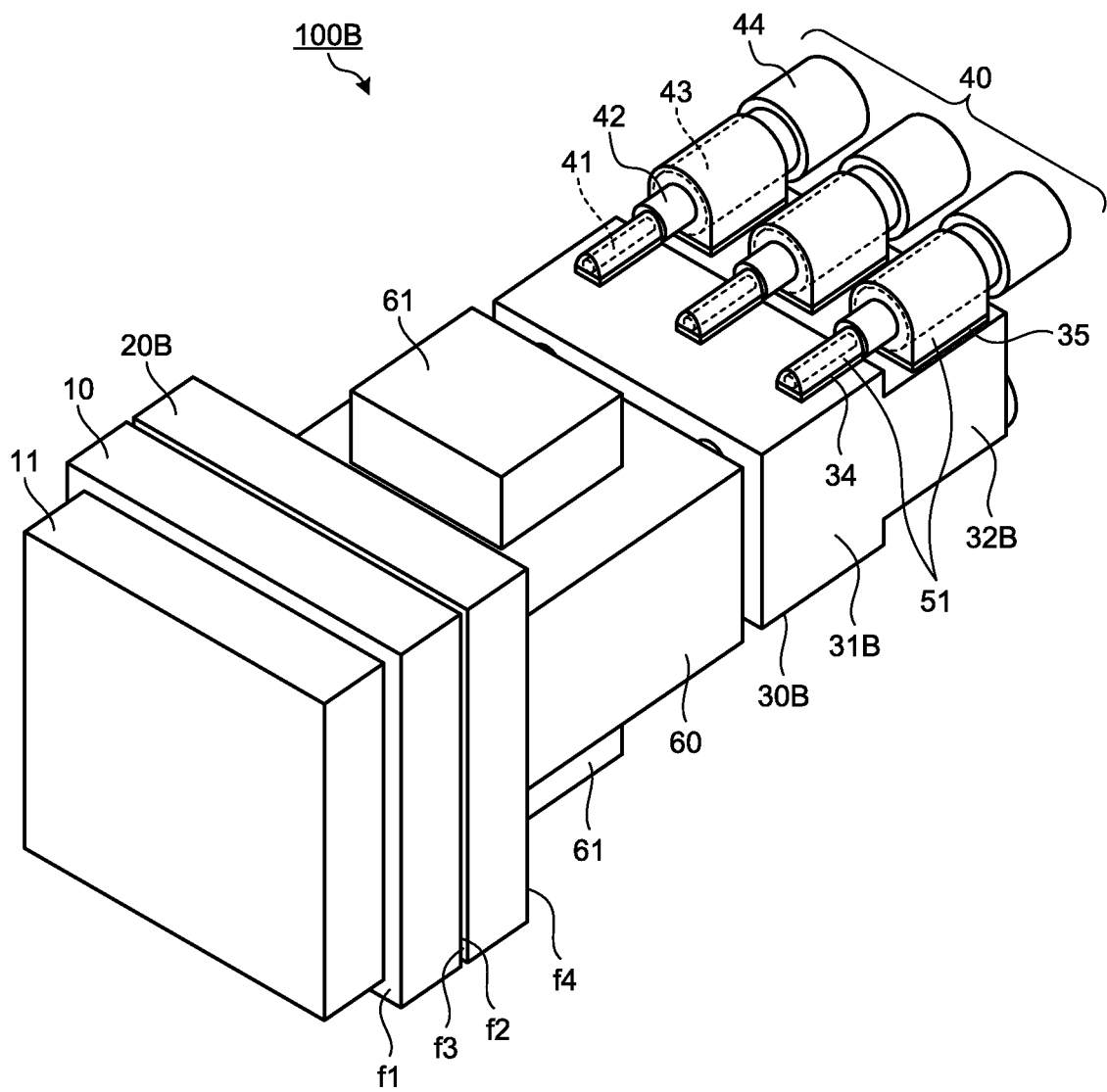
FIG. 7 is a perspective view of an imaging apparatus according to a second modification of the present embodiment.

FIG. 7 is a perspective view of an imaging apparatus according to a second modification of the present embodiment. FIG. 8 is a side view of the imaging apparatus according to the second modification of the present embodiment. In FIGS. 7 and 8, illustration of the sealing resin is omitted. In an imaging apparatus 100B according to the second modification, a cable connection substrate includes a first substrate 20B, a second substrate 30B, and a part mounting substrate 60.

The first substrate 20B has an approximately same plate shape as the imaging element 10. The first connection electrodes 21 on the front surface f3 side are electrically and mechanically connected to the sensor electrodes 12 via the bumps 13. On the back surface f4 side of the first substrate 20B, the second connection electrodes 22 are provided at connection positions of the second substrate 30B.

The part mounting substrate 60 has a rectangular column shape, and fourth connection electrodes 62 on a front surface f8 side are electrically and mechanically connected to the second connection electrodes 22 of the first substrate 20B via the bumps 23. Meanwhile, the sum of the effective conductor areas of the second connection electrodes 22 and a sum of effective conductor areas of the fourth connection electrodes 62 are approximately equal to each other. Fifth connection electrodes 65 are provided on a back surface f9 side of the part mounting substrate 60. On a top surface f10 and a bottom surface f11 serving as side surfaces perpendicular to the front surface f8 of the part mounting substrate 60, part connection electrodes 63 are provided and connected to electronic components 61 via solders 64.

On the front surface f5 side of the first main body portion 31 of the second substrate 30B, the third connection electrodes 33 are provided and electrically and mechanically connected to the fifth connection electrodes 65 of the part mounting substrate 60 via bumps 66. Meanwhile, a sum of effective conductor areas of the fifth connection electrodes 65 and the sum of the effective conductor areas of the third connection electrodes 33 are approximately equal to each other. On the top surface f6 and the bottom surface f7 serving as side surfaces perpendicular to the front surface f5 of the first main body portion 31, the core wire connection electrodes 34 are provided and connected to the core wires 41 of the coaxial cables 40 via the solders 51. In addition, on the top surface f6 and the bottom surface f7 of the second main body portion 32, the shield connection electrodes 35 are provided and connected to the shields 43 of the coaxial cables 40 via the solders 51.

In the imaging apparatus 100B according to the second modification, the sum of the effective conductor areas of the second connection electrodes 22 is set to be greater than the sum of the effective conductor areas of the first connection electrodes 21. Further, the sum of the effective conductor areas of the fifth connection electrodes 65 is set to be greater than the sum of the effective conductor areas of the fourth connection electrodes 62. Furthermore, the sum of the effective conductor areas of the core wire connection electrodes 34 and the shield connection electrodes 35 is set to be greater than the sum of the effective conductor areas of the third connection electrodes 33. With this configuration, heat generated by the imaging element 10 is likely to be discharged to the proximal end portion side while heat from the proximal end portion side is less likely to be transmitted; therefore, it is possible to reduce a thermal influence on the imaging element 10.

When manufacturing the imaging apparatus 100B according to the second modification, it is preferable to connect the first substrate 20 that has been connected to an imaging element 10B and the part mounting substrate 60 that has been connected to the second substrate 30 to which a coaxial cables 40B are connected. By connecting the first substrate 20B and the part mounting substrate 60 in a final stage, it is possible to reduce a thermal influence on the imaging element 10. Alternatively, by first connecting the first substrate 20B, the part mounting substrate 60, and the second substrate 30B, secondly connecting the cables 40 to the second substrate 30B, and finally connecting the first substrate and the imaging element 10, it is possible to reduce a thermal influence on the imaging element 10.

Further, in the imaging apparatus 100B, the first substrate 20B, the part mounting substrate 60, the electronic component 61, the second substrate 30B, the coaxial cables 40, and the sealing resin 50 (not illustrated) are positioned within the projection plane of the light receiving surface f1 of the imaging element 10. In other words, the first substrate 20B, the part mounting substrate 60, the electronic component 61, the second substrate 30B, the coaxial cables 40, and the sealing resin 50 have sizes that fall within the projection plane of the light receiving surface f1 of the imaging element 10. With this configuration, it is possible to reduce a diameter of the imaging apparatus 100B.

Third Modification

Figure 9A:
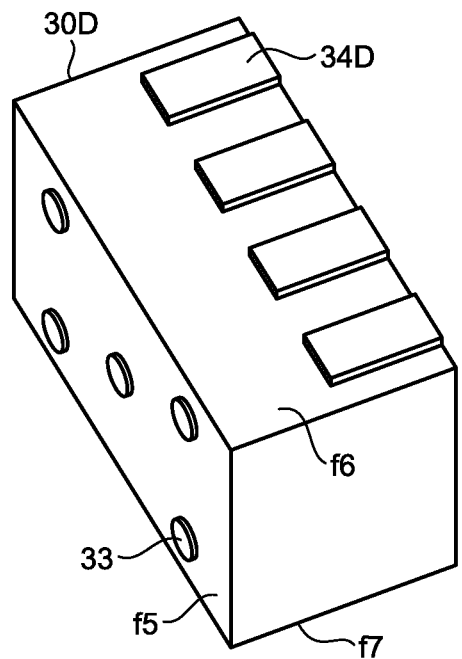
FIG. 9A is a perspective view of a second substrate according to a third modification of the embodiment of the disclosure.

FIG. 9A is a perspective view of a second substrate according to a third modification of the embodiment of the disclosure. A second substrate 30D according to the third modification is a substrate for connecting a single-wire cable. The second substrate 30D has a rectangular column shape, and is provided with the third connection electrodes 33, which are to be connected to second connection electrodes, on the front surface f5 side, and core wire connection electrodes 34D, which are to be connected to core wires of single-wire cables, on the top surface f6 side. In the third modification, a sum of effective conductor areas of the core wire connection electrodes 34D is greater than the sum of the effective conductor areas of the third connection electrodes 33. With this configuration, heat generated by the imaging element 10 is easily discharged to the proximal end portion side and heat from the proximal end portion side is less likely to be transferred; therefore, it is possible to reduce a thermal influence on the imaging element 10. While the core wire connection electrodes 34D are provided on the top surface f6 in the third modification, the core wire connection electrodes 34D may be provided on not only the top surface f6 but also the bottom surface f7 to connect single-wire cables.

Fourth Modification

Figure 9B:
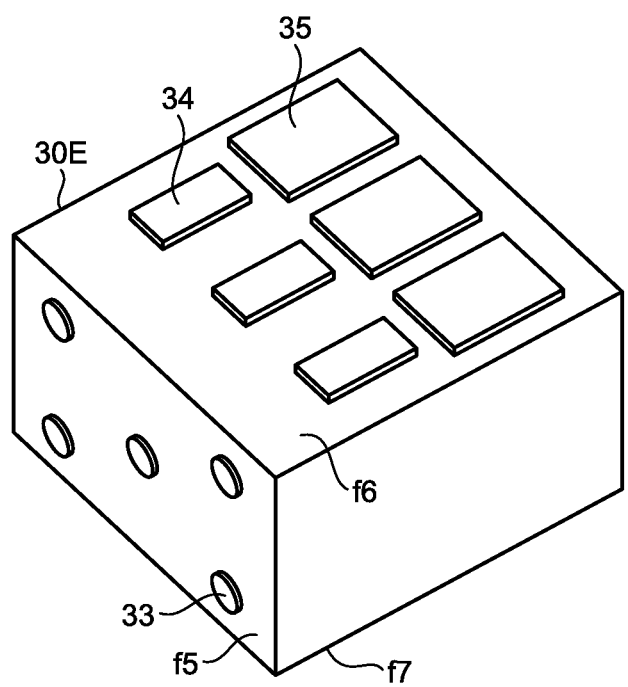
FIG. 9B is a perspective view of a second substrate according to a fourth modification of the embodiment of the disclosure.

FIG. 9B is a perspective view of a second substrate according to a fourth modification of the embodiment of the disclosure. A second substrate 30E according to the fourth modification has a rectangular column shape, and is provided with the third connection electrodes 33, which are to be connected to the second connection electrodes 22, on the front surface f5 side, and the core wire connection electrodes 34 and the shield connection electrode 35 on the top surface f6 side. In the fourth modification, the sum of the effective conductor areas of the core wire connection electrodes 34 and the shield connection electrodes 35 is greater than the sum of the effective conductor areas of the third connection electrodes 33. With this configuration, heat generated by the imaging element 10 is easily discharged to the proximal end portion side and heat from the proximal end portion side is less likely to be transferred; therefore, it is possible to reduce a thermal influence on the imaging element 10. While the core wire connection electrodes 34 and the shield connection electrodes 35 are provided on the top surface f6 in the fourth modification, the core wire connection electrodes 34 and the shield connection electrodes 35 may be provided on not only the top surface f6 but also the bottom surface f7 to connect coaxial cables.

Fifth Modification

Figure 9C:
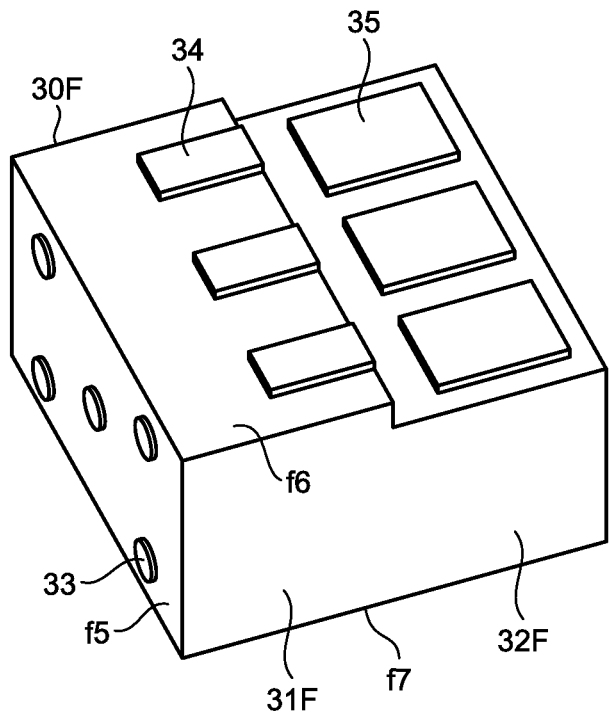
FIG. 9C is a perspective view of a second substrate according to a fifth modification of the embodiment of the disclosure.

FIG. 9C is a perspective view of a second substrate according to a fifth modification of the embodiment of the disclosure. A second substrate 30F according to the fifth modification includes a first main body portion 31F and a second main body portion 32F. A step is provided on only the top surface f6. In the first main body portion 31F, the third connection electrodes 33 to be connected to the second connection electrodes 22 are provided on the front surface f5 side, and the core wire connection electrodes 34 are provided on the top surface f6 side. Further, the shield connection electrodes 35 are provided on the top surface f6 side of the second main body portion 32F. In the fifth modification, the sum of the effective conductor areas of the core wire connection electrodes 34 and the shield connection electrodes 35 are greater than the sum of the effective conductor areas of the third connection electrodes 33. With this configuration, heat generated by the imaging element 10 is easily discharged to the proximal end portion side and heat from the proximal end portion side is less likely to be transferred; therefore, it is possible to reduce a thermal influence on the imaging element 10.

Sixth Modification

Figure 9D:
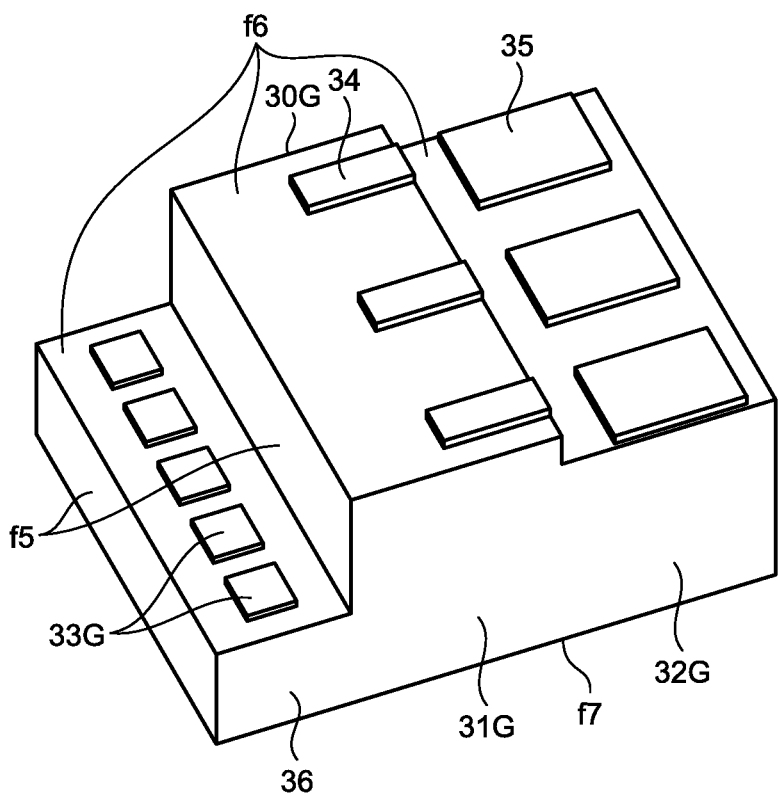
FIG. 9D is a perspective view of a second substrate according to a sixth modification of the embodiment of the disclosure.
Figure 9E:
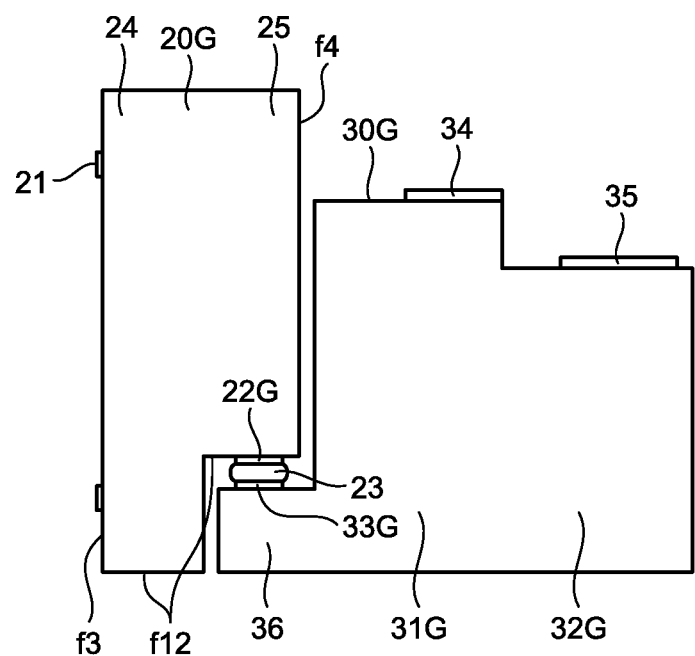
FIG. 9E is a side view illustrating connection between the second substrate illustrated in FIG. 9D and the first substrate.

FIG. 9D is a perspective view of a second substrate according to a sixth modification of the embodiment of the disclosure. FIG. 9E is a side view illustrating connection between the second substrate illustrated in FIG. 9D and the first substrate. In FIG. 9E, illustration of a sealing resin that fills a connection portion between a first substrate 20G and a second substrate 30G is omitted. The second substrate 30G according to the sixth modification includes a first main body portion 31G, a second main body portion 32G, and a third main body portion 36. The third main body portion 36 is positioned on the front surface f5 side of the first main body portion 31G, and the third connection electrodes 33G to be connected to the second connection electrodes 22 are provided on the top surface f6 side of the third main body 36.

The first substrate 20G includes a first main body portion 24 and a second main body portion 25 that is thinner than the first main body portion 24. Second connection electrodes 22G are provided on a bottom surface f12 side of the second main body portion 25, and electrically and mechanically connected to third connection electrodes 33G of the second substrate 30 via the bumps 23.

In the sixth modification, a sum of effective conductor areas of the second connection electrode 22G is set to be greater than the sum of the effective conductor areas of the first connection electrodes 21. In addition, the sum of the effective conductor areas of the core wire connection electrodes 34 and the shield connection electrodes 35 are set to be greater than a sum of effective conductor areas of the third connection electrodes 33G. With this configuration, heat generated by the imaging element 10 is easily discharged to the proximal end portion side and heat from the proximal end portion side is less likely to be transferred; therefore, it is possible to reduce a thermal influence on the imaging element 10. Furthermore, in the sixth modification, the area of a connection portion between the first substrate 20G and the second substrate 30G is increased, so that it is possible to improve a connection strength.

As described above, a cable connection electrode according to the disclosure is useful for an imaging apparatus in which a plurality of cables are connected to a substrate, in particular, preferable for an endoscope for which a size reduction is demanded.

A cable connection substrate, an imaging apparatus, an endoscope, and a method of manufacturing the imaging apparatus according to the disclosure are capable of reducing an amount of heat transferred to an imaging element while discharging heat generated by the imaging element, because the cable connection substrate includes a first substrate connected to the imaging element and a second substrate connected to a cable, and is configured such that a sum of effective conductor areas of the cable connection electrode is greater than a sum of effective conductor areas of a third connection electrode that is used for connection to the first substrate.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection substrate comprising:
a first substrate provided with, on a front surface of the first substrate, a first connection electrode to be connected to a sensor electrode of an imaging element, and provided with a second connection electrode on a back surface side of the first substrate; and
a second substrate provided with, on a front surface of the second substrate, a third connection electrode connected to the second connection electrode, and provided with, on a top surface side of the second substrate, the top surface being a side surface perpendicular to the front surface of the second substrate, a plurality of cable connection electrodes to be connected to a plurality of cables, wherein
a sum of effective conductor areas of the plurality of cable connection electrodes is greater than a sum of effective conductor areas of the third connection electrode.

2. The cable connection substrate according to claim 1, wherein a sum of effective conductor areas of the second connection electrode and the sum of the effective conductor areas of the third connection electrode are approximately equal to each other and the second connection electrode and the third connection electrode are connected via a bump,
the cable connection substrate further comprising a sealing resin disposed in a connection portion between the first substrate and the second substrate.

3. The cable connection substrate according to claim 1, wherein, on a connection surface of the first substrate and the second substrate, a contact area of the second substrate and the sealing resin is greater than the sum of the effective conductor areas of the third connection electrode.

4. The cable connection substrate according to claim 1, wherein a sum of effective conductor areas of the second connection electrode or the sum of the effective conductor areas of the third connection electrode is greater than a sum of effective conductor areas of the first connection electrode.

5. The cable connection substrate according to claim 1 wherein the plurality of cables are connected to respective cable connection electrodes that are provided on a top surface and a bottom surface of the second substrate, the top surface and the bottom surface being side surfaces that face each other.

6. The cable connection substrate according to claim 5, wherein the second substrate includes two vertically-divided substrates.

7. The cable connection substrate according to claim 1, wherein the plurality of cables are coaxial cables, each including a core wire, an internal insulator configured to cover an outer circumference of the core wire, a shield configured to cover an outer circumference of the internal insulator, and an external insulator configured to cover an outer circumference of the shield, and
the second substrate includes
a first main body portion provided with a plurality of core wire connection electrodes, and
a second main body portion which is thinner than the first main body portion and provided with one or more shield connection electrodes.

8. The cable connection substrate according to claim 2, wherein, the sealing resin having a thermal conductivity of 0.2 mW/m/K or higher.

9. An imaging apparatus comprising:
an imaging element comprising:
an image sensor configured to perform photoelectric conversion on incident light to generate an electrical signal, and
a plurality of sensor electrodes provided on a back surface opposite to a surface on which the image sensor is provided;
the cable connection substrate according to claim 1; and
a plurality of cables, wherein the cable connection substrate and the cables are positioned within a projection plane of a light receiving surface of the imaging element.

10. The imaging apparatus according to claim 9, further comprising a sealing resin disposed to cover circumferences of connection portions between the cable connection electrodes and the cables wherein the sealing resin is positioned within a projection plane of the light receiving surface of the imaging element.

11. An endoscope comprising an insertion portion provided with the imaging apparatus according to claim 9 at a distal end of the insertion portion.

12. The imaging apparatus according to claim 10, wherein, the sealing resin having a thermal conductivity of 0.2 mW/m/K or higher.

* * * * *